United States Patent [19]

Engel et al.

[11] Patent Number: 4,882,452

[45] Date of Patent: Nov. 21, 1989

[54] PROCESS FOR THE PREPARATION OF IFOSFAMIDE HAVING IMPROVED PROPERTIES

[75] Inventors: Jürgen Engel, Alzenau; Siegfried Müller, Bad Homburg; Werner Laubner, Halle, all of Fed. Rep. of Germany

[73] Assignee: Asta Pharma Akteingesellschaft, Frankfurt am Main, Fed. Rep. of Germany

[21] Appl. No.: 163,586

[22] Filed: Mar. 3, 1988

[30] Foreign Application Priority Data

Mar. 6, 1987 [DE] Fed. Rep. of Germany ....... 3707154

[51] Int. Cl.⁴ ................................................. C07F 9/24
[52] U.S. Cl. ..................................................... 558/81
[58] Field of Search .......................................... 558/81

[56] References Cited

U.S. PATENT DOCUMENTS 3,732,340  5/1973  Arnold et al. ........................ 558/81

OTHER PUBLICATIONS

Carson et al., "Lab. Text, in Organic Chemistry", (1952), p. 19.

Primary Examiner—Anton H. Sutto
Attorney, Agent, or Firm—Cushman, Darby & Cushman

[57] ABSTRACT

Ifosfamide having improved properties is obtained by crystallization from a solvent mixture selected from the group consisting of (a) a mixture of diethyl ether and a $C_1$–$C_3$ alkanol or (b) a mixture of diisopropyl ether and a $C_1$–$C_3$ alkanol under specific controlled conditions.

8 Claims, 1 Drawing Sheet

PROCESS FOR THE PREPARATION OF IFOSFAMIDE HAVING IMPROVED PROPERTIES

The present invention relates to a process for the preparation of ifosfamide having improved properties, and improved ifosfamide made by that process.

BACKGROUND OF THE INVENTION

The chemical name of the active substance ifosfamide is 3-(2-chloroethyl)-2-(chloroethylamino)-tetrahydro-2H-1,3,2-oxazaphosphorin-2-oxide, which has the formula:

$$Cl-CH_2-CH_2-NH\underset{O}{\overset{P}{\diagdown}}\underset{O-CH_2}{\overset{N-CH_2}{\diagup}}\underset{}{\overset{CH_2-CH_2-Cl}{|}}CH_2$$

In common with cyclophosphamide, ifosfamide belongs to the chemical group of oxazaphosphorins and is used therapeutically for the treatment of tumor diseases.

Ifosfamide is a white crystalline powder with a melting point of 48°–51° C. It has highly hygroscopic properties. Ifosfamide begins to sinter even below its melting point and must therefore be stored at temperatures that are as low as possible (room temperature and below). In addition, contact with moisture in the air should be avoided where possible.

The form of ifosfamide which is currently available is prone to stick together and form lumps, and to become electrostatically charged. This makes it difficult or impossible to introduce it into injection vials and to achieve accurate dosage.

In addition, the quality of ifosfamide varies from batch to batch.

SUMMARY OF THE INVENTION

The object of the invention is to prepare a form of ifosfamide which no longer displays the disadvantages described above and which, in particular, possesses better vial-filling properties.

This object is achieved in accordance with the present invention by means of the controlled recrystallization of ifosfamide in a specific solvent mixture. This solvent consists either of (a) a mixture of diethyl ether and a $C_1$–$C_3$ alkanol, preferably diethyl ether/methanol or (b) a mixture of diisopropyl ether and a $C_1$–$C_3$ alkanol, preferably diisopropyl ether/methanol, diisopropyl ether/isopropanol or diisopropyl ether/n-propanol.

The ratio of the $C_1$–$C_3$ alkanol to the ether can be between 1:1 to 1:200, preferably 1:5 to 1:200 (volume per volume). $C_1$–$C_3$ alcohols that may be used are: methanol, ethanol, propanol and isopropanol.

In the case of the form of ifosfamide which has been known hitherto, the individual crystals are generally incompletely formed with rounded edges and they are subject to very pronounced agglomerate or aggregate formation. At least 70% of the crystals of ifosfamide as known to date (for example 70–80%) display a particle size between 100 to 180 μm, where the ratio of length to width of these crystals is in the range of 3.0:1 to 3.8:1. Furthermore, ifosfamide as previously known contains a high proportion of dust (i.e. particles between 10–50 μm).

In addition, the ifosfamide as hitherto known has very poor filling properties (i.e. the dosage accuracy is poor). Dosage tests have shown the deviation of the individual values from the desired value to be, for example, between 0.9 and 6.1%, resulting in an average standard deviation of 2.29%. (Determination of standard deviation according to Muenzel, Buechi, Schultz, Galenisches Praktikum, Wissenschaftliche Verlagsgesellschaft mbh, Stuttgart, 1959).

In contrast, ifosfamide prepared according to the present invention has a maximum average relative standard deviation of 1.4%. (deviation of the individual values from the desired value at filling tests between 0.90% and 2%). As can be seen, the low scatter of the individual values is another very critical factor.

The dosage tests (filling tests) are, for example, conducted volumetrically using a screw filling machine consisting of a reservoir with a built-in stirrer (to ensure even distribution of the substance). A larger storage container is provided ahead of the reservoir, and appropriate amounts of substance—roughly prebatched—are supplied from the storage container with the aid of a dispensing meter, to match the filling speed. This ensures that the mixture of the filling material column loaded on the screw remains constant at all times and that there are no fluctuations in column height.

In this apparatus, dosage is effected by means of a screw. This screw is located in the lower opening (outlet nozzle) of the reservoir which tapers at this point.

To ensure an even composition inside the dosage area the screw widens upwards within the reservoir while the angle of the screw flight becomes simultaneously steeper, so that the screw always collects more substance than it can dose, thereby forcing any enclosed air to escape. Adherence of substance to the walls of the dosage area is avoided since the dosage area is cylindrical and the screw is so designed as to have the closest mechanically permissible tolerance.

During each filling process the screw makes the same specific and constant, preadjustable number of revolutions. This revolution count is controlled using a potentiometer (0.3–3.0 seconds) which regulates the duration of the dosage process.

This revolution count and the corresponding screw size depend on the amount to be filled in each case (dosage amount). The appropriate parameters are shown in the following table:

TABLE

| Dosage amount | Screw No. | Bore of the outlet nozzle | Filling time per dosage* |
|---|---|---|---|
| 200 mg | 10 | 4 mm | ca. 1.6 secs. |
| 500 mg | 23 | 6 mm | ca. 1.1 secs. |
| 1 g | 32 | 8 mm | ca. 1.5 secs. |
| 2 g | 33 | 8 mm | ca. 1.3 secs. |

(*)The filling times fluctuate slightly from batch to batch and must be precisely adjusted in each case.

In order to avoid trickling, the outlet nozzle of the reservoir is tapered to 0.5 mm. Trickling is then prevented by means of surface tension.

Filling occurs in a rhythmic sequence. The theoretically possible capacity is, for example, 50 fillings per minute.

A filling machine such as that described above is, for example, the penicillin filling machine of the DOS Micro type manufactured by Hoefliger and Karg, Spezialfabrik für automatische Waagen und Verpackungsmaschinen [Special factory for automatic weighing and packaging machines], Meerstrasse, Waiblingen near Stuttgart, Federal Republic of Germany.

The pH of a 10% (percent by weight) aqueous solution of the ifosfamide of the invention is 5.5 to 6 (the permissible threshold values are 4.5 to 6.5) and it is therefore suitable for therapeutic use as an injection solution without need for additional measures.

The ifosfamide obtained according to the invention consists of needle-shaped prismatic crystals (mainly elongated) having a maximum particle size of up to 450–500 um, in isolated instances up to 700 um or even 960 um. The smallest particle size is, for example, 10–20 um.

At least 70% of the crystals present (for example 70–80%) have a particle size between 80–450 $\mu$m, respectively 80–550 um, for example between 80–350 $\mu$m or between 100 350 um, respectively 80–300$\mu$m. The ratio of length to width of the crystals is from 2.5:1 to 9.5:1, in particular from 3.0:1 to 7.5:1, with this ratio in at least 70% of the crystals available (for example 70–80%) lying in a range of 3:1 to 7.5:1 (for example from 4.0:1 to 7.5:1 or 3.5:1 to 6.5:1).

The ifosfamide crystals of the invention are well developed and have no rounded edges or only slightly rounded edges. The proportion of dust (i.e. particles having a size between 10–50 $\mu$m) is low. There is little or no aggregate formation.

No electrostatic charging of the crystals is observed, for example during filling.

FIG. 1 is a photograph of the ifosfamide of the invention taken under a scanning electron microscope (SEM) at an enlargement of 100:1.

It is surprising that only recrystallization from the solvent mixture of the invention is able to yield an ifosfamide with greatly improved properties since corresponding experiments using numerous other conventional solvents and mixtures of solvents did not achieve this object. For example experiments with the following solvents failed to lead to success: water, alcohols ($C_1$–$C_4$), tetrahydrofuran, dioxan, 1,2-dimethoxyethane, dichloromethane, chloroform, 1,2-dichloroethane, 1,1,1-trichloroethane, bromoethane, methyl acetate, methyl formate, ethyl formate, 1,1,2-trichlorotrifluoroethane, acetone, ethylmethyl ketone, isobutyl methyl ketone, liquid lower hydrocarbons, mixtures of chlorinated hydrocarbons and pentane, mixtures of ketones and pentane, alcohol-pentane mixtures, ether-pentane mixtures, tert.-butylmethyl ether, 2-chloropropane, 1-chloropropane, 1-chlorobutane-methanol mixtures, 2-chlorobutane-methanol mixtures, 1-chloro-2-methyl propane-methanol mixtures, 2-chloro-2-methyl propane-methanol mixtures, 1-chloropentane-methanol mixtures, 2-chloro-2-methyl butane-methanol mixtures, fluorobenzene, toluene, propyl formate, n-butyl formate, n-butyl formate-n-butanol mixtures, isobutyl formate, isopentyl formate, ethyl acetate, isopropyl acetate, n-propyl acetate, isobutyl acetate, tert.-butyl acetate, isopropenyl acetate, methyl propionate, ethyl propionate, isopropyl propionate, mixtures of diethyl ether-methanol-isopropanolic hydrochloric acid, mixtures of 2-chloro-2-methyl propane and triethylamine.

The ifosfamide to be used in the process of the invention is the ifosfamide currently available. This ifosfamide may, for example, be manufactured according to the process of German patent No. 1 645 921.

The solvents used should be as dry as possible. Drying can, for example, be effected by distillation or other conventional drying means such as molecular sieves, magnesium sulfate, sodium sulfate and calcium chloride.

Dissolution of the ifosfamide in the solvent mixture of the invention is carried out at a temperature between 25° and 30° C. with the exclusion of moisture, appropriately with stirring (30 to 500, preferably 100 to 200 revolutions per minute) or by shaking. The solution should be just saturated or substantially supersaturated.

The ifosfamide to be used can be present in crystalline form or also in partially molten form.

For 100 g of ifosfamide, 100 to 2000, preferably 100 to 1000, in particular 150 to 700 or also 200 to 500 ml of the solvent mixture of the invention may for example be used. The volume ratio of $C_1$–$C_3$ alkanol to the appropriate ether lies preferably between 1:1 to 1:200, especially between 1:5 to 1:200.

In individual cases the ratio of alkanol to ether also depends on the total amount of the solvent mixture of the invention used in each case. For example the following ratios of alkanol to ether can be employed, depending on the amount of solvent per 100 g of ifosfamide (the temperature range in which such mixtures can, for example, be seeded, is set out in column 3 of the following table):

| ml Solvent mixture per 100 g ifosfamide | Ratio $C_1$–$C_3$ alkanol to ether | Seeding temp. |
| --- | --- | --- |
| 100–2000 | 1:1 to 1:200 | −20 to +25° C. |
| 100–1000 | 1:2 to 1:150 | −10 to +23° C. |
| 150–700 | 1:4 to 1:120 | 0 to +21° C. |
| 200–500 | 1:5 to 1:100 | +5 to +20° C. |

The volume ratio of the $C_1$–$C_3$ alkanol to the ether used in each case also depends in the individual instance on which particular alkanol-ether mixture is used. Table 1 shows as examples the corresponding volume ratios for the individual alkanol-ether mixtures as well as the preferred corresponding temperature ranges in which seeding is possible. In the case of the ranges designated b, c and d, these are preferred ranges (the letters a–d apply in each case for the entire line).

TABLE 1

| Solvent | ml solvent mixture per 100 g of ifosfamide | Ratio (ml) alkanol to ether | Seeding Temperature °C. |
| --- | --- | --- | --- |
| Diethyl ether/ methanol | (a) 100–2000 | 1:1 to 1:150 | −20 to +25 |
|  | (b) 150–600 | 1:2 to 1:100 | 0 to +23 |
|  | (c) 200–350 | 1:5 to 1:70 | +10 to +20 |
|  | (d) 230–300 | 1:10 to 1:50 | +17 to +20 |
| Diethyl ether/ ethanol | (a) 100–2000 | 1:1 to 1:150 | −20 to +25 |
|  | (b) 100–1000 | 1:2 to 1:100 | 0 to +23 |
|  | (c) 150–600 | 1:5 to 1:70 | +10 to +21 |
|  | (d) 200–350 | 1:10 to 1:50 | +15 to +20 |
| Diethyl ether/ isopropanol (& also n-propanol) | (a) 100–2000 | 1:1 to 1:200 | −20 to +25 |
|  | (b) 200–1000 | 1:5 to 1:150 | 0 to +20 |
|  | (c) 250–700 | 1:10 to 1:120 | +5 to +15 |
|  | (d) 300–450 | 1:25 to 1:100 | +8 to +12 |
| Diisopropyl ether/ methanol | (a) 100–2000 | 1:1 to 1:150 | −20 to +25 |
|  | (b) 100–1000 | 1:2 to 1:100 | −10 to +20 |
|  | (c) 150–700 | 1:4 to 1:50 | 0 to +18 |
|  | (d) 200–500 | 1:7 to 1:25 | +5 to +15 |
| Diisopropyl ether/ ethanol | (a) 100–2000 | 1:1 to 1:200 | −20 to +25 |
|  | (b) 150–1000 | 1:3 to 1:150 | −10 to +20 |
|  | (c) 200–700 | 1:5 to 1:100 | 0 to +18 |
|  | (d) 250–500 | 1:10 to 1:75 | +5 to +15 |
| Diisopropyl ether/isopropanol (& also n-propanol) | (a) 100–2000 | 1:1 to 1:200 | −20 to +25 |
|  | (b) 200–1000 | 1:5 to 1:150 | 0 to +20 |
|  | (c) 250–700 | 1:10 to 1:120 | +5 to +15 |
|  | (d) 300–450 | 1:25 to 1:100 | +8 to +12 |

The solution of ifosfamide in the ether-methanol mixture can, in addition, be treated with active carbon and/or amorphous silicic acid. 0.005 to 0.05, preferably 0.01 to 0.02 parts by weight are used per 1 part by weight of ifosfamide. The treatment with active carbon and with amorphous silicic acid is effected to remove any resinous discolorations that may be present.

Active carbons that may be used are, for example: animal charcoal as well as activated plant-wood charcoal prepared by pure steam activation and optionally brought to a very low ash content through post-treatment with mineral acid and deionized water, i.e. vegetable active carbons which are characterized by low heavy metal contents at low total ash content. Such carbon powders fulfill for example the requirements of DAB 8 (West) (DAB=Deutsches Arzneibuch, 8th Edition dated 1978) or the European Pharmacopoeia 2. Polycyclic hydrocarbons cannot be detected within the prescribed limits. Medicinal carbon powder according to DAB 8 (West) having the following pore distribution is, for example, suitable:
micropores (diameter 0–20 Å): 0.6 ml/g
mesopores (diameter 20–300 Å): 0.15 ml/g
macropores (diameter greater than 300 Å): 0.5 ml/g In addition, washed (i.e. post-treated with mineral acid and deionized water) and powdered decolorizing active carbons can be considered which fulfill the requirements of the DAB 8 with regard to ash content, heavy metal content and fluorescent materials and which do not have such a fine pore structure as medicinal carbon. Such decolorizing active carbons have, for example, the following pore distribution:
micropores: 0.2–0.4 ml/g, in particular 0.4 ml/g
mesopores: 0.2–0.5 ml/g, in particular 0.2 ml/g
macropores: ca. 0.5 ml/g, in particular 0.5 ml/g.

Decolorizing active carbons of this type are, for example, prepared by Degussa Aktiengesellschaft and are sold under the registered trade marks EPONIT (for example EPONIT 114 Spezial, EPONIT 113 Spezial, carbons neutralized with phosphoric acid such as EPONIT 113 Np, EPONIT 114 Np), Carbopuron and Degusorb.

0.005 to 0.05, preferably 0.01 to 0.02 parts by weight of amorphous silica gel are used per 1 part by weight of ifosfamide.

The amorphous silicic acid that can, for example, be used is kieselguhr, silica gels such as, for example, synthetically prepared, highly porous amorphous silicic acid in the form of hard grains having a grain size of 0.15 to 10 mm. A grain size of 0.15 to 0.30 mm is particularly favorable. The water content may, for example, be up to 10%. The specific surface can be up to 650 $m^2/g$. It is generally about 400 $m^2/g$. The bulk weight can be up to 650 g/l. A bulk weight of 450 to 500 g/l is favorable.

Kieselguhr is particularly preferred.

Treatment with active carbon and amorphous silicic acid takes place at 20° to 40° C., preferably 25° to 30° C. for 5 to 60, preferably 10 to 40, in particular 15 to 20 minutes with movement of the ifosfamide solution, for example by stirring or shaking.

Once the ifosfamide solution has been separated from the adsorbants, for example by means of filtration, the solution is brought to the seeding temperature, preferably with an internal temperature lying above 11° C., in particular between 14° and 20° C. This cooling occurs in known manner, for example by means of methanol/dry ice or thermostats in a period between 10 to 600, preferably 20 to 20 minutes.

The seeding of the ifosfamide solution so obtained is carried out with pure ifosfamide, with 0.01 to 5, preferably 0.1 to 0.5 parts by weight of seed crystals being used per 100 parts by weight.

The ifosfamide used for seeding purposes may, for example, be obtained according to German patent No.1 645 921 (Example 4). It is important that the ifosfamide used for seeding is totally crystalline or at least contains markedly crystalline portions.

Pure seed crystals can, for example, also be obtained by transferring a sample of the ifosfamide solution in the solvent mixture of the invention into a glass vessel, cooling (for example to 0° C.) and occasionally triturating with a glass rod, optionally adding a little pure diethyl ether. Precipitation of the crystals then occurs within, for example, 30 minutes to one week.

After seeding, the solution is kept under constant movement (for example stirring with a speed of revolution of 30 to 150, preferably 50 to 80 revolutions/minute) for 1 to 72, preferably 3 to 48, in particular 8 to 24 hours at an internal temperature of −20° to +25° C., preferably +5° to +20° C., in particular +11° to +20° C. or +14° to +20° C. and subsequently optionally cooled slowly and evenly, i.e. in controlled manner, with constant movement or constant stirring to −10° to +5° C., preferably −5° to +5° C., in particular −5° to 0° C.

This cooling is effected through correspondingly even reduction in the temperature of the cooling bath, for example over a period of from 8 to 72, preferably 8 to 30 hours. Cooling occurs in linear manner, for example with the aid of a programmed thermostat.

After the seeding, the ifosfamide begins to crystallize out. The stirring speed after the seeding and also during the subsequent cooling should be carried out in such a way that the crystals formed do not settle too much on the bottom. The stirring or movement should be such that the crystals are just kept in motion and prevented from settling.

The filtering off of the precipitated ifosfamide crystals is effectively carried out under inert atmosphere and with the exclusion of moisture, for example under a dry inert gas (for example nitrogen, an inert gas such as argon or also air with a relative humidity of less than 25%) and under a pressure of, for example, 0.1 to 3 bar.

The ifosfamide crystals separated by filtration may be washed with dry diethyl ether or another substance (such as, for example, hydrocarbons with 5 to 7 carbon atoms) after which they are suctioned off. At this stage, it is advisable to blow a dry inert gas (such as those mentioned above) through the crystals for 0.1 to 10, preferably 0.5 to 2 hours, during which time the crystals should have about the same temperature as that to which they were previously cooled. A temperature rise of up to 10° C. can optionally be permitted. This temperature can, for example, be adjusted by cooling the filter assembly to the previously given temperature and/or cooling the inert gas to this temperature.

The removal of the residual solvent is carried out in a gentle manner at a temperature of between 0° and 40° C., preferably 10° and 25° C. under a vacuum of 0.1 to 100, preferably 1 to 20 mbar, while the crystal mass is kept in slow movement, for example by slow or occasional stirring (for example 6 to 20 revolutions/minute). When a rotary evaporator is used this can, for example, be achieved by allowing it to revolve during the first 6 hours for 1 to 2 minutes every hour and subsequently only switching on the rotation for 1 to 2 minutes every 2 to 3 hours.

The time required for this drying is, for example, 5 to 100, preferably 20 to 50 hours.

DETAILED DESCRIPTION OF PREFERRED EMBODIMENTS

Example 1

1400 g of ifosfamide (crude product prepared according to Example 4 of German patent No. 1 645 921) are dissolved under stirring and exclusion of moisture in a mixture of 3280 ml of dried diethyl ether and 80 ml of methanol (analytical grade) at 26° C. (solution is cloudy). 13 g of active carbon and 6.5 g of kieselguhr are then added and stirred for 60 minutes at 27°–30° C. The adsorbents are subsequently filtered off using a pressure filter (cloudy solution) and the mother liquor is transferred to a 6 liter plane ground joint reaction vessel (with built in anchor screw, thermometer, ascending tube with drying tube, cooling jacket and outlet spindle on the bottom of the vessel), cooled to an internal temperature of 17.1° C. (temperature of cooling bath 17° C.), the solution seeded with 5 g of crystalline ifosfamide[1] at a stirrer revolution speed of 80 revolutions/minute, stirred for 24 hours at an internal temperature of 17° C. and then evenly cooled to 0° C. for 24 hours, whereupon the ifosfamide crystallizes out. The crystals so obtained are placed on a cooled pressure filter (0° C.), suctioned off with nitrogen and rewashed twice with 2000 ml of diethyl ether cooled to 0° C.; subsequently nitrogen is blown through the filter layer for 1 hour (temperature of the pressure filter 0° C.). The crystals are then transferred to a 6 liter pear-shaped flask and dried on a rotary evaporator at room temperature for 30 hours at 6 revolutions/minute (occasionally switched on for 1–2 minutes) and dried at 10–20 mbar.

[1] Obtained according to Example 4 of German Patent No. 1,645,921.

Yield: 1204 g (86% of theory)

The ifosfamide so obtained has a needle-shaped prismatic crystalline form; a maximum particle size up to 480 um, in isolated instances up to 700 um, with 70 to 80% of the crystals present having a particle size between 150–350 um. The proportions of the crystals (length:width) are: from 3.0:1 to 7.5 (or also 9.3):1. In 70 to 80% of the crystals present, the ratio of length to width is 3.5:1 to 8.0:1.

The crystals are well formed (only slightly rounded edges). The proportion of dust is small.

Example 2

60 kg of ifosfamide (crude product) are dissolved in 160 liters of diethyl ether and 10 liters of methanol at 30° C. Following the addition of 600 g of active carbon (Eponit), the mixture is stirred. The batch is then filtered and crystallized as follows:

Cooled to 17° C. with stirring for 1.5 to 2.0 hours and then seeded with 200 g of ifosfamide.

The temperature of 17° C. is maintained for 12 hours, then the temperature is lowered to 15° C. during 10 hours. Linear fall in temperature to 0° C. during 18 hours.

Temperature of 0° C. is maintained for 6 hours.

During these processes the stirring speed is changed according to the following schedule:
first 4 hours at 32 revolutions/minute
then ca. 2 hours at 42 revolutions/minute
then ca. 14 hours at 55 revolutions/minute
then ca. 28 hours at 65 revolutions/minute.

The crystallizate is then transferred to a suction filter and the mother liquor suctioned off under a nitrogen atmosphere. The mixture is then rinsed twice with, in each case, 20 liters of diethyl ether, the solvent is removed and finally the crystals are press dried for 1 hour under nitrogen. The substance is transferred to a mixing dryer and dried according to the following method:

Predrying for about 3 hours in a water jet pump vacuum. Mixer running continuously.

About 45 hours end drying under an oil pump vacuum. Mixer on interval running (duration of interval 5 seconds/hour).

Yield: 46 kg of about 77% excl. mother liquor substance

Melting point 48.9° C.

Fillability (standard deviation)=0.94%. (Good fillability at standard deviations of 1.0 to 1.5%).

Example 3

1400 g of ifosfamide (crude product) are dissolved in a mixture of 3280 ml of dried diisopropyl ether and 400 ml of dried methanol at 30° C. 10 g of active carbon are added to the solution and the mixture is stirred for 60 minutes at 30° C.

The active carbon is filtered off using a pressure filter and the mother liquor transferred to a 6 liter plane ground joint reaction vessel with built in anchor screw, thermometer, ascending tube with drying tube, cooling jacket and outlet spindle on the bottom of the vessel.

Th solution is then cooled within 15 hours to 5° C. with a stirrer operating at 80 revolutions/minute and seeded at this temperature with 10 g of crystalline ifosfamide at this temperature (slowly commencing crystallization). Stirring continues for 5 hours at 5° C. internal temperature, followed by even, linear cooling for one hour to 0° C. and stirring for 36 hours at 0° C.

The ifosfamide that has crystallized out is placed on a cooled pressure filter (of 0° C.) and pressed with nitrogen. Rewashing is carried out twice with 2000 ml of dry isopropyl ether cooled to 0° C. Nitrogen is then blown through the filter layer for 1 hour (temperature of the pressure filter 0° C.).

The crystals are then dried for 36 hours in a 6 liter pear-shaped flask on a rotary evaporator at room temperature at a pressure of 10–20 mbar (rotation of the rotary evaporator 6 revolutions per minute, occasionally switched on for 1 to 2 minutes).

The yield is 795.8 g (about 57% of theory).

The melting point of the ifosfamide so obtained is 49–50%.

Example 4

46 kg of ifosfamide (crude product) are dissolved in a mixture of 160 liters of diisopropyl ether and 2 liters of isopropanol at 27° C. The mixture is then cooled to +10° C. during 3 hours and seeded at this temperature with 0.16 kg of crystalline ifosfamide. The mixture is then stirred for 16 hours at a temperature between 7° and 10° C. (50 revolutions/minute). This is followed by linear, even cooling for 0 hours to 0° C.

As described in the preceding example, the ifosfamide is sucked off, washed, sucked off under nitrogen and the solvent removed in the mixer dryer.

Melting point: 49° C.

Yield: 35.5 kg=72.2%.

What is claimed:

1. Needle-shaped prismatic crystalline ifosfamide characterized by the following properties:
   (a) at least 70% of the crystals have a particle size between 150–550 μm, the individual crystals have a ratio of length to width of 3.5:1 to 8:1, and
   (b) the crystals have a maximum average relative standard deviation or the deviation of the individual values from the desired value at filling tests between 0.90% and 2% of 1.4%.

2. A process for the preparation of ifosfamide having improved properties, which comprises the steps of:
   (a) forming a solution of ifosfamide in a solvent mixture selected from the group consisting of i. a mixture of diethyl ether and a $C_1$–$C_3$ alkanol and ii. a mixture of diisopropyl ether and a $C_1$–$C_3$ alkanol, the volume ratio of the $C_1$–$C_3$ alkanol to the ether being 1:1 to 1:200, and the proportion of solvent mixture being 100 to 2000 ml per 100 g of ifosfamide.
   (b) seeding the solution with pure ifosfamide at a temperature between −20° to +25° C. with stirring, the stirring being continued for several hours at the seeding temperature,
   (c) optionally cooling the solution in step (b) evenly by stirring over a period of 8 to 48 hours to a temperature between 0° C. to −5° C., provided that the temperature is above 0° C. when seeding takes place, and
   (d) isolating and drying the resulting crystals.

3. A process according to claim 2 wherein the solvent mixture in step (a) is a mixture of diethyl ether and methanol.

4. A process according to claim 2 or claim 3 wherein the seeding in step (c) takes place at a temperature greater than 11° C.

5. A process according to claim 2 or claim 3 wherein the seeding takes place at a temperature between 14° and 20° C.

6. A process according to claim 2 or claim 3 wherein cooling from the seeding temperature to the filtering temperature is carried out by using a cooling bath which is in thermal contact with the solution to obtain a controlled, even, and linear temperature reduction.

7. A pharmaceutical composition comprising a pharmaceutically effective amount of ifosfamide according to claim 1 and a pharmaceutical carrier or medium.

8. An aqueous solution of ifosfamide according to claim 1 having a pH of 5.5 to 6 containing 10% by weight of the crystals which is suitable for therapeutic use as an injection solution.

* * * * *